United States Patent [19]

Haber et al.

[11] Patent Number: 4,813,426
[45] Date of Patent: Mar. 21, 1989

[54] SHIELDED SAFETY SYRINGE HAVING A RETRACTABLE NEEDLE

[75] Inventors: Terry M. Haber, Lake Forest; Clark B. Foster, El Toro; William H. Smedley, Lake Elsinore; John A. Lewis, Jr., Costa Mesa, all of Calif.

[73] Assignee: Habley Medical Technology Corporation, Laguna Hills, Calif.

[21] Appl. No.: 118,745

[22] Filed: Nov. 9, 1987

[51] Int. Cl.⁴ ............................................. A61B 5/00
[52] U.S. Cl. ................................... 128/763; 604/198; 604/232
[58] Field of Search ............... 604/192, 193, 196, 198, 604/263, 232; 128/763–765

[56] References Cited

U.S. PATENT DOCUMENTS 4,170,993  10/1979  Alvarez ........................... 604/198 X
4,425,120   1/1984  Sampson et al. ..................... 604/198

Primary Examiner—John D. Yasko
Attorney, Agent, or Firm—Morland C. Fischer

[57] ABSTRACT

A shielded safety syringe comprising a cylindrical, outer protective sleeve, an inner needle carrier movable axially through the sleeve, and a double-ended hypodermic needle supported by the needle carrier and aligned coaxially with respect to the outer sleeve and needle carrier. The needle communicates with an evacuated blood collection tube at the interior of the outer sleeve. A position control button is connected to the needle carrier and slidable through an axial guide channel formed in the outer sleeve for moving the needle carrier between proximal and distal positions within the sleeve. Accordingly, the needle is also moved through the outer sleeve to be relocated from an axially extended position, at which to make a veni puncture through a targeted tissue area, to a retracted position, at which the needle is completely surrounded and shielded by the outer sleeve to permit a safe handling and disposal of the syringe while avoiding an accidental needle strike. Locking detents are formed at opposite ends of the guide channel to receive the position control button, so that the needle maybe reliably retained in either the axially extended or retracted position.

12 Claims, 2 Drawing Sheets

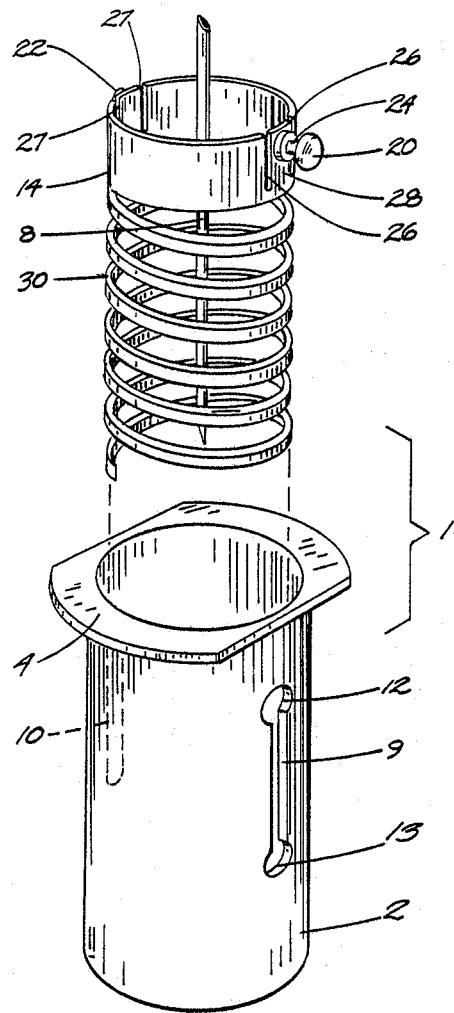
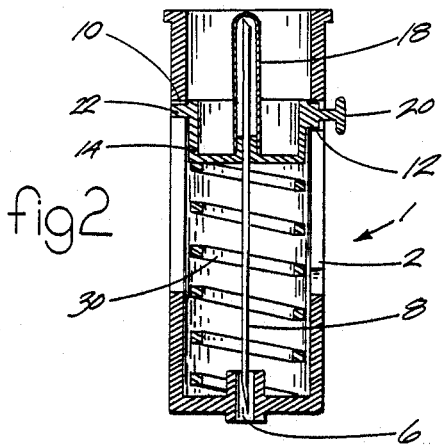
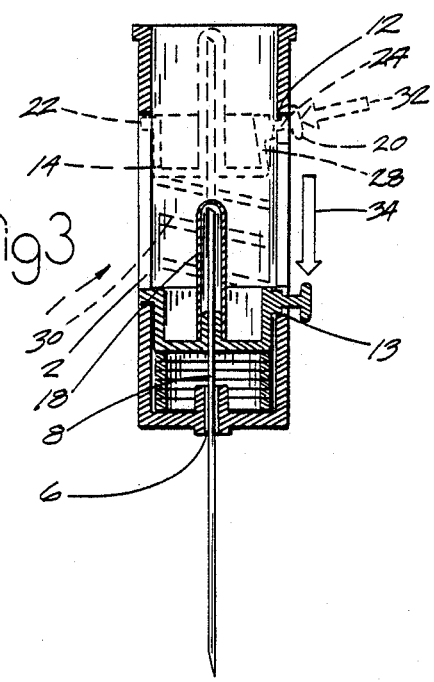
fig1
fig2
fig3

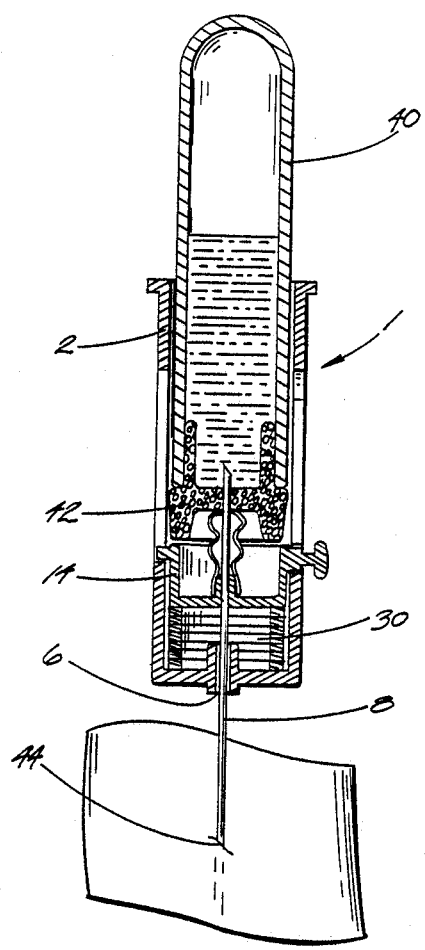
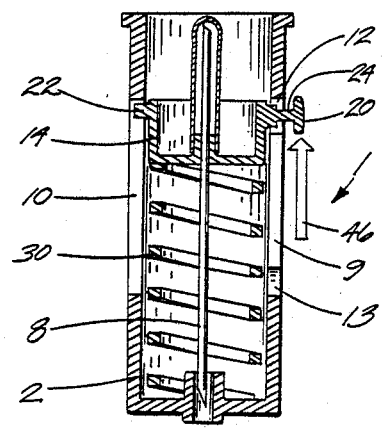
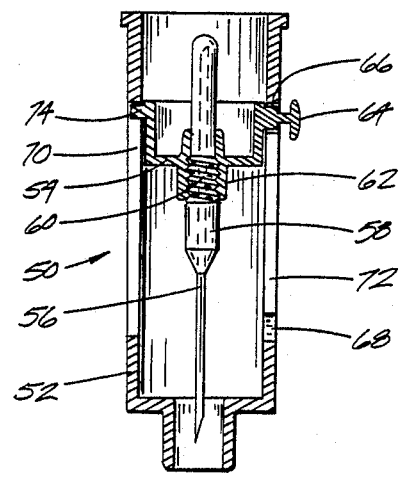
fig 4
fig 5
fig 6

SHIELDED SAFETY SYRINGE HAVING A RETRACTABLE NEEDLE

BACKGROUND OF THE INVENTION

1. Field of the Invention

This invention relates to a shielded safety syringe having an outer protective sleeve and a retractable needle which communicates with an evacuated blood collection tube at the interior of the sleeve. The needle may be relocated from an axially extended position relative to the outer sleeve, at which to draw a sample of blood through a targeted tissue area, to a retracted position, at which the needle is completely surrounded and shielded by the outer sleeve to avoid an accidental needle strike.

2. Prior Art.

Hypodermic syringes are used for a variety of purposes. By way of example, the syringe may be used for vacuum tube phlebotomy, where one or more samples of a patient's blood are successively drawn into respective evacuated blood collection tubes by way of a double ended hypodermic needle. Such a syringe may be used to treat a patient having a communicable disease. Prior to disposal of the syringe, the hypodermic needle is sometimes broken to prevent reuse. Health care workers are especially susceptible to accidental and potentially infectious needle strikes due to the careless handling or breaking of the needle and disposing of the syringe after use. The resulting mini-accidents caused by the accidental needle strike typically require a blood test for such diseases as AIDS and hepatitis. The corresponding cost and inefficiency of testing health care workers who have received an inadvertent needle strike result in considerable waste, which may be particularly damaging to a health care facility which is striving for economy.

The following U.S. patents provide examples of syringes having a hypodermic needle which may be shielded after use to prevent an accidental needle strike:

U.S. Pat. No. 2,571,653, Oct. 16, 1951
U.S. Pat. No. 4,356,822, Nov. 2, 1982
U.S. Pat. No. 4,425,120, Jan. 10, 1984
U.S. Pat. No. 4,631,057, Dec. 23, 1986

However, in the known shielded syringes, an outer sleeve is moved axially relative to a fixed hypodermic needle for either exposing or shielding the needle. Such shielded syringes are unlike the safety syringe which is disclosed below, where a hypodermic needle is moved axially relative to the fixed, outer protective sleeve, such that the needle may be relocated between axially extended and retracted positions.

SUMMARY OF THE INVENTION

In general terms, a shielded safety syringe is disclosed comprising a cylindrical outer protective sleeve, a cylindrical inner needle carrier movable axially through the sleeve, and a double ended hypodermic needle supported by the needle carrier, such that the needle is aligned coaxially with respect to the outer sleeve and inner carrier. The needle extends proximally through the outer sleeve for communication with an evacuated blood collection tube which is to be infused with a sample of a patient's blood. The needle carrier includes an integral guide tab and position control button which extend from opposite sides of the carrier. The guide tab and position control button are received in and slidable through respective guide channels which extend axially through opposite sides of the outer sleeve. Proximal and distal locking detents are formed at opposite ends of the guide channel in which the position control is received to retain the needle carrier, and the needle supported thereby, at relatively proximal or distal positions within the outer sleeve.

In operation, the position control button is moved out of the proximal locking detent and through its respective guide channel for receipt at the distal locking detent. Accordingly, the needle carrier is moved axially through the outer sleeve towards the distal end thereof, such that the needle is moved to an axially extended position relative to the sleeve in order to make a veni puncture through a targeted tissue area of the patient and thereby permit a blood sample to be automatically dranw into the blood collection tube. After the blood sample has been taken and the blood collection tube removed from the outer sleeve, the position control button is moved out of the distal locking detent and through its respective guide channel for receipt at the proximal locking detent. Accordingly, the needle carrier is moved axially through the outer sleeve towards the proximal end thereof, such that the needle is relocated to a retracted position relative to the sleeve. A compression spring may be included within the outer sleeve to automatically drive the needle carrier, and the needle supported thereby, towards the proximal end of the outer sleeve when the position control button is moved out of the distal locking detent. Hence, the needle is retracted into the outer protective sleeve to be completely surrounded and shielded by the sleeve to permit the syringe to be safely handled and discarded while avoiding the possibility of an accidental needle strike and the spread of a contagious, and possibly life threatening, disease.

BRIEF DESCRIPTION OF THE DRAWINGS

FIG. 1 is an exploded view of a shielded safety syringe which forms the present invention;

FIG. 2 is a cross-section of the syringe of FIG. 1 with a hypodermic needle thereof located at a retracted position relative to an outer protective sleeve;

FIG. 3 is a cross-section of the syringe of FIG. 1 with the hypodermic needle located at an axially extended position relative to the outer protective sleeve;

FIG. 4 shows the syringe of FIG. 1 with the needle in an axially extended position for making a veni puncture through a targeted tissue area, so that an evacuated blood collection tube may be automatically infused with a blood sample;

FIG. 5 shows the syringe of FIG. 4 with the needle relocated to the retracted position relative to the outer sleeve after a blood sample has been collected and the blood collection tube removed; and FIG. 6 shows an alternate embodiment of a shielded safety syringe.

DESCRIPTION OF THE PREFERRED EMBODIMENTS

The shielded safety syringe which forms the present invention is now disclosed while referring to the drawings, where FIG. 1 shows the syringe 1 including a hollow (e.g. molded plastic) outer protective sleeve 2 having an open proximal end and a substantially closed distal end. A flange 4 extends around the open proximal end to facilitate the handling and operation of syringe 1. A narrow opening 6 (best shown in FIGS. 2 and 3) is formed in the distal end of sleeve 2 to accommodate one end of a souble ended hypodermic needle 8. A pair of axially aligned guide channels 9 and 10 are formed through opposing sides of the outer sleeve 2. One of the channels (e.g. 9) includes coextensively formed proximal and distal locking detents 12 and 13, the purpose of which will soon be described. The diameter of detents 12 and 13 is larger than the width of guide channel 9.

Safety syringe 1 also includes an inner (e.g. flexible molded plastic) spring-biased, cylindrical needle carrier 14 having an open proximal end and a substantially closed distal end. Coaxially aligned with the needle carrier 14 is a double ended hypodermic needle 8. As is best shown in FIGS. 2 and 3, needle 8 is molded to and retained by the closed distal end of needle carrier 14, such that one end of needle 8 extends distally through outer sleeve 2 and distal opening 6 for making a veni puncture in the skin of a patient, while the opposite end extends proximally through sleeve 2 to communicate with an evacuated blood collection tube (shown in FIG. 4). A protective sheath 18 is placed over the proximally extending end of needle 8 to preserve the sterility thereof prior to communication with the blood collection tube.

Extending radially from opposite sides of needle carrier 14 are a position control button 20 and guide tab 22. As will soon be explained, position control button 20 and guide tab 22 are adapted to be received in and slide through the axial guide channels 9 and 10, respectively, of outer sleeve 2 for the important purpose of controlling the position of needle 8 relative to outer protective sleeve 2. To this end, position control button 20 includes a relatively narrow stem 24 located between relatively wide and oppositely disposed shoulder and finger pad portions. A pair of short, parallel aligned, and axially extending slots 26 are formed through needle carrier 14 at opposite sides of position control button 20 to permit button 20 to be rotated (as is best illustrated in FIG. 3) into the locking detents 12 and 13 of guide channel 9 for controlling the axial movement of needle carrier 14 and, accordingly, the position of needle 8 relative to outer sleeve 2. That is to say, a flexible locking spring 28 is established between axial slots 26 by which to normally bias the relatively wide shoulder portion of position control button 20 into receipt by either the proximal or locking detent 12 or 13. As will soon be explained, the position control button 20 can be rotated into detent 12 or 13 to move the shoulder portion thereof out of receipt by detent 12 or 13 and thereby permit button 20 to slide through guide channel 9 and needle carrier 14 (and needle 8 supported thereby) to be relocated from the proximal end towards the distal end of outer sleeve 2 or vice versa.

A pair of short, parallel aligned and axially extending slots 27 are also formed through needle carrier 14 at opposite sides of guide tab 22 to permit guide tab 22 to be rotated slightly during the assembly of syringe 1 when the needle carrier 14 is received at the interior of and aligned concentrically with the outer sleeve 2. That is, and as is best shown in FIGS. 2 and 3, a spring is established by which to normally bias guide tab 22 into receipt by guide channel 10 to stabilize the needle carrier 14 during relocation between the poximal and distal ends of outer sleeve 2.

A helical compression spring 20 is received within outer sleeve 2 between the closed distal end thereof and the needle carrier 14, such that hypodermic needle 8 and compression spring 20 are coaxially aligned with one another. As is best shown in FIG. 2, compression spring 20 applies an axial and proximally directed force upon needle carrier 14 so that needle carrier 14 is normally biased towards the proximal end of outer sleeve 2, whereby needle 8 is correspondingly retained in a retracted position within sleeve 2. The embodiment illustrated in FIG. 1 shows the compression spring 30 as a separate and discretely formed component of syringe 1. However, it is to be understood that one end of spring 30 may otherwise be coextensively connected to and formed as an integral extension of the needle carrier 14.

In FIG. 2 of the drawings, the syringe 1 is shown in an assembled configuration with compression spring 30 in a relaxed state for biasing needle carrier 14 towards the proximal end of outer protective sleeve 2, such that hypodermic needle 8 is retained at a retracted position relative to sleeve 2. Referring concurrently to FIGS. 1 and 2, position control button 20 is received through the proximal locking detent 12 of guide slot 9 and guide tab 22 is received through the guide channel 10, whereby the needle carrier 14 is retained at a proximal position within outer sleeve 2. More particularly, the relatively wide shoulder portion of position control button 20 is located in proximal locking detent 12. Position control button 20 is blocked from sliding distally through guide channel 9, inasmuch as the diameter of the shoulder portion of button 20 is larger than the width of guide channel 9. Hence, the needle carrier 14 is locked at a relatively proximal position, such that needle 8 is retracted within and completely surrounded by the outer protective sleeve 2.

In FIG. 3 of the drawings, the needle carrier 14 is relocated towards the distal end of outer protective sleeve 2 against the bias of compression spring 30, whereby spring 30 is compressed and hypodermic needle 8 is moved to an axially extended position relative to the sleeve 2. More particularly, and referring concurrently to FIGS. 1 and 3, a radially directed force (represented by reference arrow 32 of FIG. 3) is applied (e.g. by means of the user's thumb) to the finger pad portion of position control button 20 to depress button 20 into the proximal locking detent 12 of guide channel 9 and thereby cause locking spring 28 to rotate in a relatively inward direction (illustrated in phantom). Accordingly, the relatively narrow stem 24 of position control button 20 is moved into proximal locking detent 12. With the position control button 20 depressed and the stem 24 thereof located in detent 12, the button 20 is slid (e.g. by means of the user's thumb) axially and distally through channel 9 (in the direction of reference arrow 34), whereby to relocate needle carrier 14 from a relatively proximal position (illustrated in phantom) towards the distal end of outer sleeve 2. At the same time, the guide tab 22 of needle carrier 14 slides axially and distally through guide channel 10 to stabilize the relocation of needle carrier 14.

After needle carrier 14 is relocated to a distal position in outer sleeve 2, the user terminates the application of the radially directed force (i.e. removes his thumb) from the finger pad portion of button 20. Accordingly, the spring memory of locking spring 28 will cause spring 28 to rotate in a radially outward direction, so as to automatically return the relatively wide shoulder portion of position control button 20 to distal locking detent 13. Position control button 20 is now blocked from sliding proximally through guide channel 9, inasmuch as the diameter of the shoulder portion is larger than the width of channel 9. Hence, the needle carrier 14 is locked at a distal position, such that the needle 8 is advanced through the distal opening 6 of outer sleeve 2 to the axially extended position relative to sleeve 2 for drawing blood from the vein of a patient. Moreover, the spring 30 is compressed between needle carrier 14 and the distal end of outer sleeve 2 to store potential energy for a purpose that will be described when referring to FIG. 5.

Details of the operation of syringe 1 and the retractable needle 8 thereof for infusing a blood collection tube with a sample of a patient's blood are disclosed while referring to FIGS. 4 and 5 of the drawings. FIG. 4 shows the syringe 1 having an evacuated blood collection tube 40 received through the open proximal end of outer protective sleeve 2. The blood collection tube 40 may be a conventional evacuated tube which is common to the pactice of vacuum tube phlebotomy, or tube 40 may be that described in the copending patent application No. 118,759 filed Nov. 9, 1987 and entitled "MANUALLY EVACUATED SUCTION TUBE" by Terry M. Haber et al.

In FIG. 4, inner needle carrier 14 is located at a distal position within outer sleeve 2 (in a manner that has already been described while referring to FIG. 3), such that spring 30 is compressed and needle 8 is retained at an axially extended position relative to sleeve 2. That is, the proximal end of needle 8 extends through a rubber stopper to communicate with the interior of blood collection tube 40, and the distal end of needle 8 extends through the opening 6 at the closed distal end of outer sleeve 2 to make a single veni puncture through a targeted tissue area 44 of the patient. Accordingly, one or more samples of the patient's blood are automatically drawn into successive collection tubes 40 via needle 8. When the last blood sample has been taken, the needle 8 is withdrawn from the targeted tissue area 44, and the blood collection tube 40 is removed from the outer sleeve 2, so that the blood sample can be centrifuged and studied.

Referring now to FIG. 5 of the drawings, the needle 8 is retracted within the outer sleeve 2, so that the syringe 1 may be safely discarded while avoiding the potential for exposing a health care worker to an accidental needle strike and the spread of a contagious, and possibly life threatening, disease. More particularly, the position control button 20 is depressed at the finger pad portion thereof, whereby to cause the locking spring (designated 28 in FIG. 3) of needle carrier 14 to rotate inwardly and thereby locate the relatively narrow stem 4 of button 20 within distal locking detent 13. Inasmuch as the diameter of stem 24 is less than the width of guide channel 9, the button 20 is free to slide through channel 9 while the guide tab 22 slides through guide channel 10. That is to say, the potential energy stored by spring 30 while in a compressed state (of FIG. 4) will cause spring 30 to return to its normal, relaxed state so as to automatically drive needle carrier 14, and the needle 8 retained thereby, axially and proximally through outer sleeve 2 in the direction of reference arrow 46.

After needle carrier 14 is relocated to a proximal position in sleeve 2, the user releases the position control button 20, whereby the normal bias of the locking spring 28 (of FIG. 3) will cause button 20 to rotate in a radially outward direction so as to automatically return the relatively wide shoulder portion of button 20 to proximal locking detent 12 (as is illustrated in FIG. 5 and as was previously described when referring to FIG. 2). Position control button 20 is now blocked from sliding distally through guide channel 9, inasmuch as the diameter of the shoulder portion thereof is larger than the width of channel 9. Hence, the needle carrier 14 is locked at a proximal position, such that the needle 8 is retained at the retracted position relative to outer protective sleeve 2.

Therefore, it will be recognized that a positive, self-locking feature is established when the relatively wide shoulder portion of position control button 20 is received in proximal locking detent 12. Hence, a disposal cartridge is created (in FIG. 5) having the needle carrier 14 locked in a proximal position and the needle 8 retained in a retracted position relative to outer protective sleeve 2. The needle 8 is completely surrounded and shielded by outer sleeve 2, so that the syringe 1 may be safely handled while avoiding the potential for an accidental needle strike and the possible spread of a contagious disease.

FIG. 6 of the drawings shows an alternate embodiment for a shielded safety syringe of the present invention. Like the syringe 1 of FIGS. 1-5, the syringe 50 of FIG. 6 includes an outer protective sleeve 52 and an inner needle carrier 54. A double ended hypodermic needle 56 is retained at a substantially closed distal end of needle carrier 52. However, needle 56 is a well-known and commercially available needle including a centrally disposed hub 58 and a screw threaded portion 60. The screw threaded portion 60 of needle 56 is adapted to be received by a hollow, screw threaded neck 62 which extends through the closed distal end of needle carrier 54. Accordingly, the syringe 50 may be advantageously interfaced with a conventional and readily available double ended needle by merely screwing portion 60 of needle 56 into the threaded neck 62 of carrier 54.

Moreover, the compression spring (designated 30 in FIGS. 1-5) is eliminated from the syringe 50 of FIG. 6 so as to reduce the number of component parts and the corresponding cost of syringe manufacture. Without the aforementioned compression spring (i.e. to automatically drive needle carrier 54 axially and proximally through outer sleeve 52), the syringe user manually relocates the needle carrier 54 from a distal position towards a proximal end of outer sleeve 2 (or vice versa) by first depressing position control button 64 into the distal locking detent 68, then sliding button 64 and guide tab 74 through respective guide channels 72 and 70, and finally repositioning button 64 in proximal locking detent 66 (in a manner similar to that which was previously described when referring to FIG. 5). Accordingly, the needle carrier 54 is moved axially and proximally through outer sleeve 52, whereby the needle 56 thereof is safely retained at the retracted position relative to sleeve 52.

It will be apparent that while preferred embodiments of the present invention have been shown and described, various modifications and changes may be made without departing from the true spirit and scope of the invention. For example, while evacuated tube 40 of FIG. 4 has been described as a blood collection tube, it is to be understood that tube 40 could otherwise have application for aspirating a wound, draining a boil, aspirating a snake bite, and the like.

Having thus set forth a preferred embodiments of the invention, what is claimed is:

1. A phlebotomy syringe including an outer sleeve having a partially open distal end and an open proximal end through which to receive a blood collection tube to be infused with a blood sample, said syringe further comprising:

a hypodermic needle having first and second ends;

means for carrying said needle located within said outer sleeve such that a first end of said needle projects outwardly and distally from said sleeve for penetrating a targeted tissue area and the second end of said needle extends proximally and inwardly into said sleeve for communication with the blood collection tube, said needle carrying means having a position control button connected thereto; and guide channel means formed in said sleeve between the distal and proximal ends thereof, the button of said needle carrying means being received in and slidable through said guide channel means for relocating said needle carrying means and the needle carried thereby relative to the interior of said sleeve.

2. The syringe recited in claim 1, wherein said guide channel means has oppositely disposed proximal and distal locking detents, the position control button of said needle carrying means being located at said distal locking detent, such that the first end of said needle projects outwardly and distally from said outer sleeve, said button being slidable through said guide channel means to be located in said proximal locking detent to relocate said needle carrying means to a relatively proximal position in said sleeve and thereby retract the first end of said needle so as to be completely surrounded and shielded by said sleeve.

3. The syringe recited in claim 2, wherein the proximal and distal locking detents of said guide channel means have a larger linear dimension than the corresponding linear dimension of said guide channel means.

4. The syringe recited in claim 2, further comprising a pair of parallel, axially aligned slots formed in said needle carrying means at opposite sides of said position control button to establish flexible spring means by which said position control button may be rotated through said proximal or distal locking detent and slid through said guide channel means.

5. The syringe recited in claim 1, further comprising compression spring means located between the distal end of said outer sleeve and said needle carrying means for biaisng said needle carrying means towards the proximal end of said sleeve.

6. The syringe recited in claim 2, wherein said needle carrying means also has a guide tab connected thereto, said guide channel means including first and second channels formed in said outer sleeve, said position control button and said guide tab being received in and slidable through respective ones of said first and second channels for relocating said needle carrying means relative to the interior of said sleeve.

7. A phlebotomy syringe comprising an outer protective sleeve having a partially open distal end and an open proximal end through which to receive a blood collection tube to be infused with a blood sample, needle carrying means located within and movable through said outer sleeve, a double ended hypodermic needle retained by said needle carrying means at the interior of said outer sleeve, one end of said needle communicating with the blood collection tube at the interior of said outer sleeve, and means for moving said needle carrying means through the interior of said outer sleeve so that the second end of said needle may be located at either an axially extended position projection through the partially open distal end of said outer sleeve or a retracted position completely surrounded and shielded by said outer sleeve.

8. The syringe recited in claim 7, wherein the means for moving said needle carrying means through the interior of said outer sleeve includes a guide channel formed in and extending between the proximal and distal ends of said outer sleeve and a position control button extending from said needle carrying means to be received in and slidable through said guide channel.

9. The syringe recited in claim 8, further comprising proximal and distal locking detents located at opposite ends of said guide channel for receiving said position control button and thereby retaining the second end of said needle at either the axially extended or retracted position relative to said outer sleeve.

10. The syringe recited in claim 7, further comprising compression spring means located between the distal end of said outer sleeve and said needle carrying means for biasing said needle carrying means towards the proximal end of said sleeve.

11. The syringe recited in claim 8, wherein said outer sleeve includes an additional guide channel extending between the proximal and distal ends thereof, said needle carrying means also having a guide tab extending therefrom to be received in and slidable through said additional guide channel for stabilizing the movement of said needle carrying means through said outer sleeve.

12. The syringe recited in claim 9, further comprising spring means for biasing said positio control button into one of said locking detents, said position control button being movable against the bias of said spring means and through said locking detents for moving said needle carrying means through said outer sleeve.

* * * * *